United States Patent [19]

Moon et al.

[11] Plant 5,155

[45] Dec. 13, 1983

[54] ROSE CV. AROCLIDD

[75] Inventors: Joseph L. Moon, Wasco; Jack E. Christensen, Ontario, both of Calif.

[73] Assignee: Armstrong Nurseries, Inc., Ontario, Calif.

[21] Appl. No.: 394,479

[22] Filed: Jul. 1, 1982

[51] Int. Cl.[3] ..... A01H 5/00

[52] U.S. Cl. ..... Plt./2

[58] Field of Search ..... Plt./2

*Primary Examiner*—Robert E. Bagwill

*Attorney, Agent, or Firm*—Synnestvedt & Lechner

[57] ABSTRACT

A climbing sport of the hybrid tea, Double Delight.

1 Drawing Figure

1

This invention relates to a new variety of rose cv. Aroclidd. The plant is a climber and originated as a bud sport of the rose cv. "Double Delight" (U.S. Plant Pat. No. 3,847).

The sport was discovered by Joseph L. Moon growing in the fields of a commercial nursery in Wasco, Calif. and was first propagated by budding on Dr. Huey understock by Jack E. Christensen in Ontario, Calif. Subsequent reproduction of the plant by budding at both Wasco, Calif. and Ontario, Calif. have shown that the sport is stable in its essential characteristics and holds its distinguishing characteristics through succeeding propagations.

The characteristics of the sport are substantially identical to those of the patent Double Delight as described in U.S. Plant Pat. No. 3,847 except as hereinafter noted.

The accompanying drawing is a black and white photograpgh of a 3 year old plant of the rose cv. Aroclidd growing outdoors in Ontario, Calif. that was taken in late February (early March) and shows the climbing habit of the sport.

2

Aroclidd is a climber, whereas the parent rose Double Delight is of the hybrid tea class.

Aroclidd has long, strong canes that obtain an overall length of about 8 to 10 feet, whereas the canes of the parent rose Double Delight is a bush of upright spreading habit but not especially tall growing.

The parent rose cv. Double Delight blooms nearly continuously on current season's wood during the growing season. In contrast, Aroclidd flowers predominantly on second season's wood with a large flowering flush in spring followed by intermittent flowering during the remainder of the growing season.

We claim:

1. A new and distinct variety of rose as a sport of the rose cv. Double Delight (U.S. Plant Pat. No. 3,847) characterized in that it is a climber and flowers on second season's wood, with a large flowering flush in the spring followed by intermittent flowering during the remainder of the growing season and otherwise having the characteristics of the parent rose Double Delight.

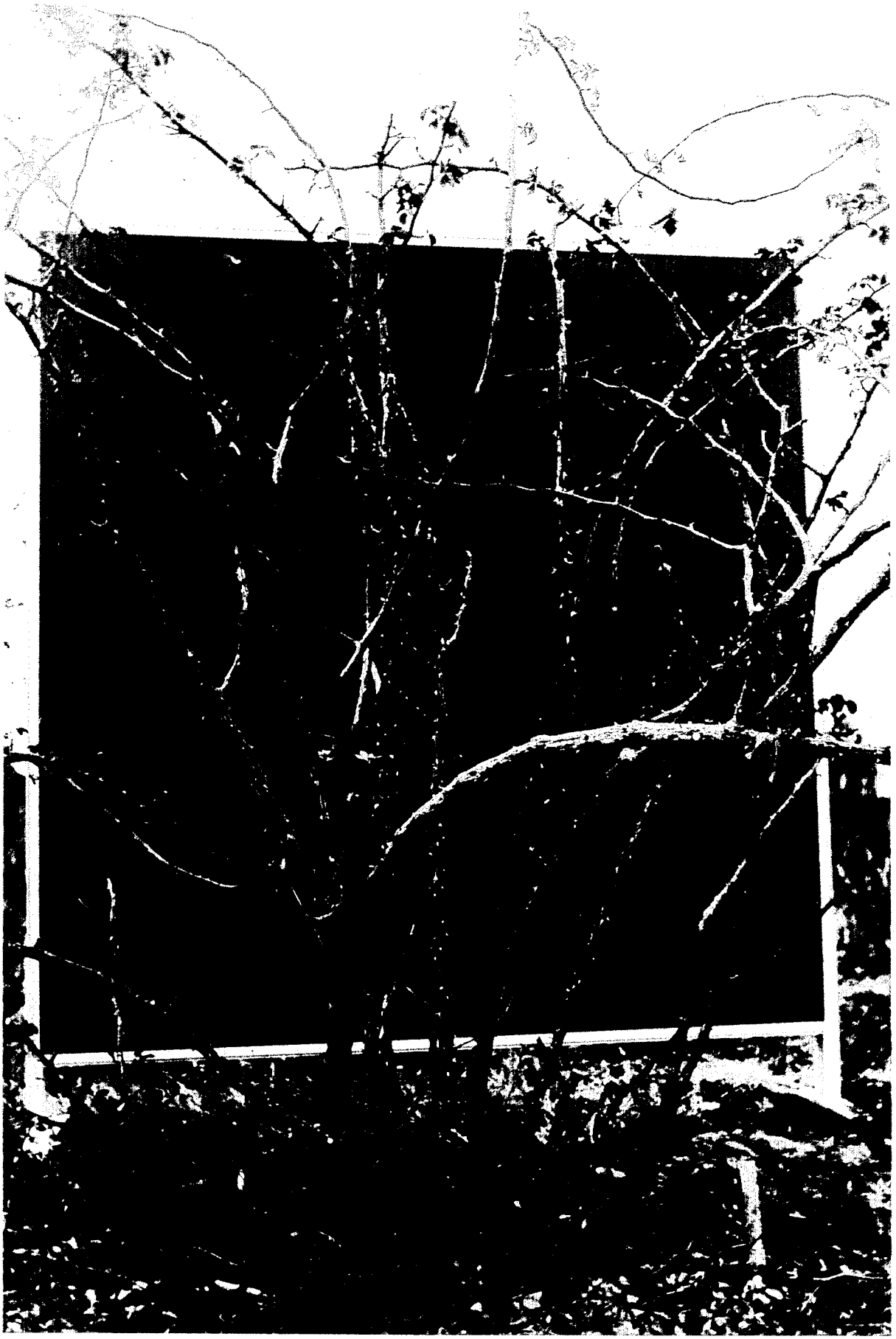

* * * * *